United States Patent [19]

Sun

[11] Patent Number: 5,419,358

[45] Date of Patent: May 30, 1995

[54] GAS MONITORING SYSTEM FOR A BOILER

[75] Inventor: Yung Sun, New York, N.Y.

[73] Assignee: Francis Myrtil, Far Rockaway, N.Y.

[21] Appl. No.: 100,446

[22] Filed: Aug. 2, 1993

[51] Int. Cl.⁶ .............................................. F16K 17/36
[52] U.S. Cl. ...................................... 137/78.4; 340/634
[58] Field of Search ............................ 137/78.4; 340/634

[56] References Cited

U.S. PATENT DOCUMENTS

| | | |
|---|---|---|
| 2,637,331 | 5/1953 | Sullivan . |
| 2,812,770 | 11/1957 | Sullivan . |
| 2,873,753 | 2/1959 | Sullivan . |
| 3,733,595 | 5/1973 | Benedict ............................ 340/634 |
| 3,955,186 | 5/1976 | Green et al. . |
| 4,007,456 | 2/1977 | Paige et al. ......................... 340/634 |
| 4,088,986 | 5/1978 | Boucher ............................. 340/634 |
| 4,098,284 | 7/1978 | Yamada . |
| 4,207,912 | 6/1980 | Ichikawa . |
| 4,219,806 | 8/1980 | Enemark . |
| 4,231,249 | 11/1980 | Zuckerman . |
| 4,369,647 | 1/1983 | Shigemori et al. . |
| 4,384,925 | 5/1983 | Stetter et al. . |
| 4,443,793 | 4/1984 | Hall, Jr. ............................ 340/634 |
| 4,490,715 | 12/1984 | Kusanagi et al. .................. 340/634 |
| 4,766,762 | 8/1988 | Tsan . |
| 4,787,410 | 11/1988 | Fujieda et al. . |
| 4,912,338 | 3/1990 | Bingham . |
| 4,992,965 | 2/1991 | Hölter et al. ........................ 340/634 |

Primary Examiner—A. Michael Chambers
Attorney, Agent, or Firm—Philip Furgang

[57] ABSTRACT

A gas monitoring system for use with a gas-fired boiler in a house or the like. The boiler is supplied with flammable gas. The system comprises a transducer, a visible and audible alarm circuit, a digital access terminal, an exhaust fan, and alarm systems, which may be audible or visual. Leaked gas is detected by a gas transducer which produces a voltage indicative of the presence of gas. An electronic circuit, which comprises a comparator, buffer, and power transistor, receives the voltages from the transducer and, when a predetermined level of voltage is received, turns on and closes two switches. One switch enables an audio alarm and provides power to a second switch. The second switch, when closed, joins a source of power to a visual alarm (a bulb), turns on an exhaust fan, and closes a normally open solenoid valve. The solenoid valve is in the gas-conveying conduit. Closing the valve shuts off the unwanted flow of gas. The first switch is provided with a manual reset switch for resetting the system.

23 Claims, 2 Drawing Sheets

GAS MONITORING SYSTEM FOR A BOILER

BACKGROUND OF THE INVENTION

This invention relates to a gas monitoring system which may be used in connection with a furnace or boiler to protect against unwanted gas leakage.

DESCRIPTION OF THE PRIOR ART

It is clearly desirable to detect the presence of a gas leak in the location where a furnace or boiler may be located. The build of gas can result in explosion or, if at lower levels, illness. Most gas-fired devices work automatically. The owner of such a device, such as a boiler, seldom takes care of it.

One prior art gas detector is disclosed by Bingham in U.S. Pat. No. 4,912,338 entitled "Safety System for a Gas Operated Appliance in a Vehicle". Bingham discloses a safety system comprising an exhaust fan, a gas sensor, and a solenoid operated valve which is adapted to automatically and mechanically close to the flow of gas through a gas line in the event of an interruption of electric current or any other emergency. The valves will close when a predetermined voltage does not pass through each of them. However, gas leaks from a gas-fired boiler mainly because of the malfunction of the igniter and/or the controller of the normally-closed valve. When there is an electrical failure, the normally closed valve will remain closed and gas cannot leak from the boiler. As a consequence, electrical failure is not a primary concern in control of the flow of leaking gas. This system has no means for turning off the flow of gas when gas is detected.

Shigemori, et al., in U.S. Pat. No. 4,369,647, entitled "Gas Leakage Detector" discloses a device for giving an alarm in the presence of an unwanted gas. Stetter, et al., in U.S. Pat. No. 4,384,925, entitled "Gas Sensing Unit with Automatic Calibration Method" describes a self calibrating device for giving an indication of the presence of a gas. The disclosed devices provide no means for controlling the flow of gases.

SUMMARY OF THE INVENTION

It is an object of this invention to provide a sensing and control device that will interrupt the flow of gas in a conduit when concentrations of gas in the atmosphere exceed a predetermined value.

It is an object of this invention to provide a sensing and control device which will shut down a gas conduit to prevent explosions from occurring when gas exceeds a predetermined level in the atmosphere.

It is yet another object of this invention to detect a gas leak and shut off gas flow before the gas reaches a level of concentration which can be subject to explosion.

It is still another object of this invention to provide an alarm means for sounding an audible, visual, or recordable alarm indicating that an undesirable level of flammable gas has accumulated.

It is yet another object of this invention to provide an exhaust fan for removing undesired concentrations of flammable gas upon detection of this concentration.

It is still another object of this invention to provide a device for detecting the presence of a gas leakage and shutting down a gas conduit which is inexpensive in operation, comprising few parts, and efficient in the use of electrical power.

In accordance with the teachings of this invention there is provided a gas sensing and control device of the type for use with a gas conduit for channeling gas to a heating device or the like, the sensing and control device comprises transducer means for sensing the concentration gas in the air and providing voltage indicative of the gas concentration. There is also provided electronic circuit means which is responsive to the transducer means. The electronic circuit means provides at least two logic signals which indicate of whether or not the concentration of the gas has exceeded a predetermined level. There is also provided valve control means, operatively connected to the gas conduit and responsive to the electronic circuit means, for closing or opening the gas conduit in response to one of said two logic signals to thereby close the flow of the gas in the conduit when the gas concentration exceeds the predetermined level.

DESCRIPTION OF THE PREFERRED EMBODIMENT

Figure 1:
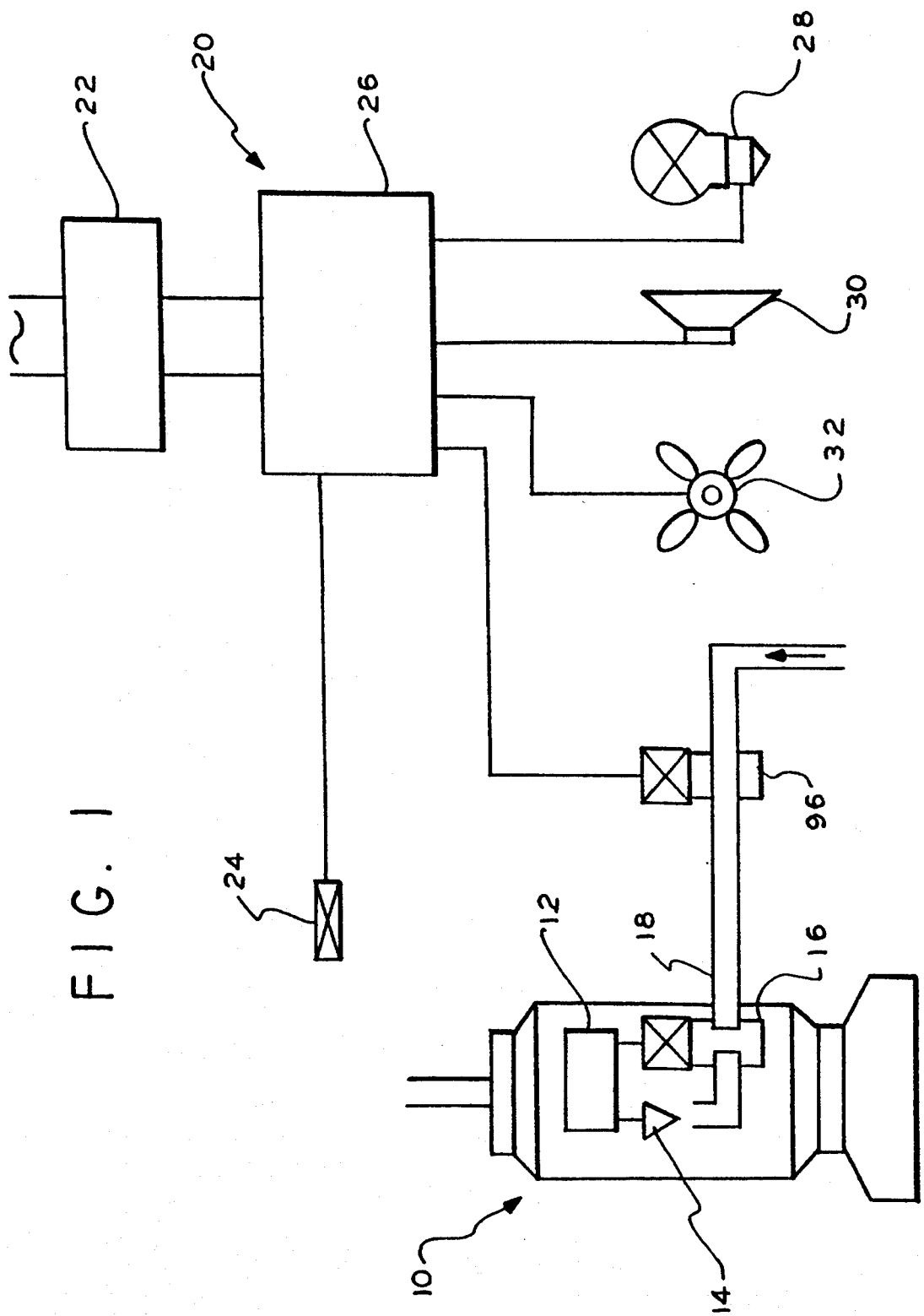
FIG. 1 is a block diagram of the gas monitoring system constructed in accordance with this invention.
Figure 2:
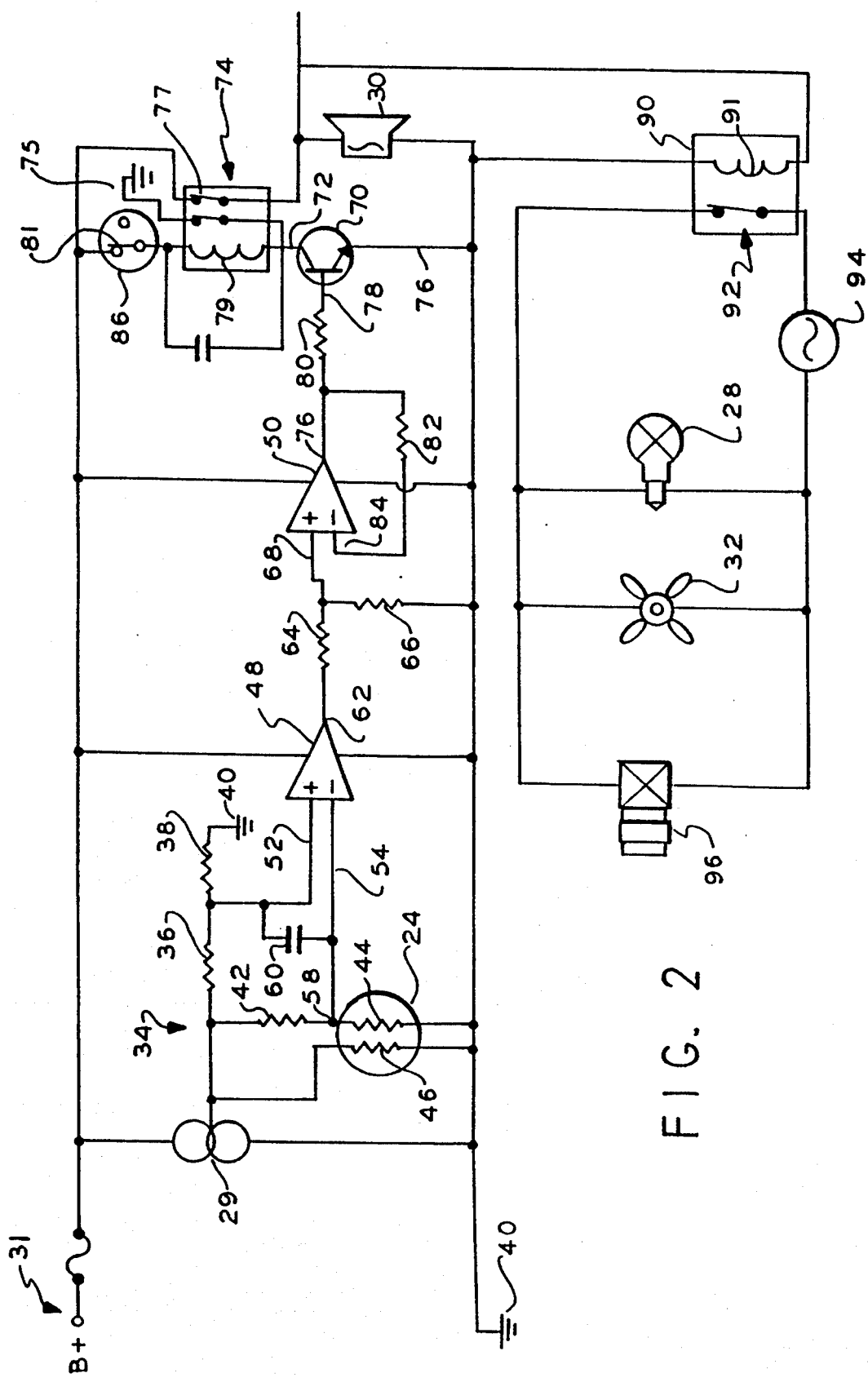
FIG. 2 is a schematic of the electronic circuit of this invention.

This invention may be used in any setting. Typically, it is best used in an infrequently accessed area, such as a basement. In this example, there is shown in a block diagram (FIG. 1) a boiler 10, which is of a well-known construction. The boiler 10 may comprise a control panel 12, an igniter 14, and a control valve 16. A conduit 18 may convey an flammable fluid, such as natural gas to the boiler 10 and through the control valve 16. Typically, if there is an electrical failure, the boiler valve 16 will close, shutting off the flow of gas to the boiler 10 in the conduit 18. One general problem with this configuration is that there is no means for shutting off the flow of gas when there is no electrical failure. The result can be catastrophic.

The gas monitoring system 20 of this invention may preferably comprise a power supply 22, a gas transducer 24, and a control unit 26. The system 20 may further comprise any one or a number of warning or safety devices. These may include, for example, a light bulb 28, an audio speaker 30, or a fan 32.

The control unit 26 of this invention comprises a voltage regulator 29 for providing a source of voltage to the system 20. The regulator 29 is connected across a source of DC voltage (B+) 31 and ground 40. Preferably, the voltage supplies is 12 VDC or 24 VDC. The regulator 28 is preferably a Motorola MC7805 which provides 5 VDC. This voltage is applied across a voltage divider 34. The divider 34 comprises series connected resisters 36, 38 which are connected to ground 40 in parallel with a resistor 42 in series with one resistive element 44 of the transducer. 24. The series connected resistor 42 and element 44 are in series with ground 40. The transducer 24 may be, for example, a TGS813 by Figaro Engineering, Inc. The other element 46 is connected in parallel with the resistor 42 and element 44 from the source 28 to ground 40.

Two operational amplifiers 48 and 50, well known in the art, which may, for example, be derived from a dual LM358N by Motorola. On input 52 of the first operational amplifier 48 may be coupled to the juncture 54 of the series connected resistors 36, 38. The other input 56 of the amplifier 48 may be coupled to the juncture 58 of resistor 42 with element 44. A filter capacitor 60 is connected across the inputs 52 and 54 of the operational amplifier 48 to provide stability and filter out high frequency noise.

The output 62 of the operational amplifier 48 is divided across two resistors 64, 66 to ground 40 and to the input 68 of the second operational amplifier 50. The second operational amplifier 50 serves as a unit-gain buffer to drive a power transistor 70. The transistor 70 may be, for example an MPS2222N by Motorola. The collector 72 of the transistor 70 may be coupled to a solid state switch 74. The emitter 76 of the transistor 70 is connected to ground 40. The output 76 of the second operational amplifier 50 is coupled to the base 78 through a resistor 80. Another resistor 82 couples the output 76 to an input of the amplifier 50. The switch 74 may comprise at least two normally open switch contacts 75, 77 and means for controlling the state of the switches, shown schematically as a coil 79. The coil 79 connects the collector 72 to the normally closed contact 81 of a manual switch 86. The other side of the contact 81 is connected to the B+. One normally open contact 75 of the switch 74 is connects, when closed, the collector 72 to ground 40.

In operation, the general purpose transducer 24 of the type having high sensitivity to methane, propane, and butane and low sensitivity to gases which not of concern, such as cooking fumes. The transducer 24 is selected so that its resistive element 46 can be used to heat the gas sensing element 44. As is well known in the art, when a combustible gas comes into contact with the sensing element 44, the resistivity of the sensing element 44 increases. The sensitivity is predetermined by the supplier of the transducer 24.

The resistor 42 in series with the first element 44 of the transducer 24 is chosen to establish the desired voltage across the transducer. This voltage in this example may be 3.4 VDC. Resistors 36 and 38 are chosen so that there is a constant voltage across Resistor 38 which will be equal to the upper level of voltage across the transducer element 44 at the threshold when gas is to be detected. In this case, this voltage may be 2.5 VDC.

The first operational amplifier 48 is used as a comparator. As such, the output voltage is either 0 or approximately 12 VDC. The output voltage of the comparator 48 is divided across resistors 80 and 82 so that the power transistor 70 may be appropriately driven. As thus described, the transistor 70 is either ON or OFF. In these states, the transistor 70 controls the switch positions of the solid state switch 74.

When no gas is sensed, the differential input 52 is negative and the output voltage is 0. This keeps the transistor 70 turned OFF. As a consequence, the solid state switch 74 is de-energized, the switch contacts are open and no B+ will reach the speaker 30, fan 32 or light bulb 28. The fan 32 may be used to exhaust unwanted concentrations of gas from the area.

When there is a gas leak from the boiler 10 or some other source, and the concentration exceeds a predetermined value, the resistor of element 44 is reduced. The resulting drop in voltage causes the first operational amplifier 48 to be turned on and provide an output voltage which may be approximately 12 VDC. The value of resisters 64, 66, and 82 are so chosen so that the 12 VDC will turn transistor 70 ON. The current flow through the transistor 70 causes the normally open switch contacts 75 and 77 of switch 74 to close. The switch contact 77 is connected on one side to the B+ and on the other side to the speaker system 30 which is in parallel with the switch closing means (shown schematically as a coil) 91 of a second solid state switch 90 and in series to ground 40. The normally open switch contact 92 of the switch 90 is connected in series with a source of AC voltage 94 and in parallel with the lamp 28 and fan 32 and a normally open valve 96. The normally open valve 96 is in series with the conduit 18 (FIG. 1). When gas is sensed, the two switches 90 and 74 close. An audible alarm may be provided through the speaker system 30, the light bulb 28 may light, and the exhaust fan 32 to turn. Most important, the normally open valve 96 will close, turning off the flow of gas. To reset the system, the manual switch 86 is opened, placing the switch 74 at ground. The collector 72 of the transistor 70 is now connected to ground 40. The speaker system 30 is disconnected from the B+. The second switch 90 opens, disconnecting the flow of current from the bulb 28, fan 32, and reopening the valve to thereby reset the system. If gas remains, however, the system 20 will reactivate and issue the alarm again. The output 88 of the speaker 30 may also serve as a signal to be received by a computer (not shown) for logging the status of the system.

From the above description, it will thus be seen that there has been provided a new and novel gas sensing device for eliminating the flow of gas.

It is understood that although there has been shown the preferred embodiment of the invention that various modifications may be made in the details thereof without departing from the spirit as comprehended by the following claims.

What is claimed is:

1. A gas sensing and control device operated by a source of electricity and being of the type for use with a gas conduit for channeling gas to a heating device or the like, said sensing and control device comprising:
    a) transducer means for sensing the concentration gas in the air and providing voltage indicative thereof;
    b) electronic circuit means, responsive to said transducer means, for providing at least two logic signals indicative of whether or not the concentration of the gas has exceeded a predetermined level; and
    b) valve control means, connected to the gas conduit so as to, in an operative condition, close the conduit thereby preventing the flow of the gas; said valve control means being operative in response to one of said two logic signals from said electronic circuit means when the gas concentration exceeds said predetermined level.

2. A gas sensing and control device as recited in claim 1 wherein said circuit means further comprises device means for providing information in response to said logic signals.

3. A gas sensing and control device as recited in claim 2 wherein said device means is a light system for providing a visual alarm when the gas concentration exceeds said predetermined level.

4. A gas sensing and control device as recited in claim 2 wherein said device means is an exhaust system for causing the removal of the gas when the gas concentration exceeds said predetermined level.

5. A gas sensing and control device as recited in claim 2 wherein said device means is a computer for storing said logic signals.

6. A gas sensing and control device as recited in claim 2 wherein said device means is an audio speaker system for providing an audible alarm when the gas concentration exceeds said predetermined level.

7. A gas sensing and control device as recited in claim 2 wherein said circuit means further comprises comparator means, responsive to said transducer means, for comparing said voltage provided by said transducer with a predetermined base voltage and providing at least one logic signal indicating that the gas concentration exceeds said predetermined level of concentration.

8. A gas sensing and control device as recited in claim 7 wherein said circuit means further comprises logic amplifier means, responsive to said comparator means, for providing one of two logic signals indicating whether the gas concentration is below or above said predetermined level.

9. A gas sensing and control device as recited in claim 8 wherein said circuit means further comprises switch means, responsive to said amplifier means, for causing said valve means to close the conduit when the gas concentration exceeds said predetermined level.

10. A gas sensing and control device as recited in claim 9 further comprises device means, responsive to said switch means, for providing information in response to said logic signals.

11. A gas sensing and control device as recited in claim 10 wherein said device means is an audio speaker system for providing an audible alarm when the gas concentration exceeds said predetermined level.

12. A gas sensing and control device as recited in claim 10 wherein said device means is a light system for providing a visual alarm when the gas concentration exceeds said predetermined level.

13. A gas sensing and control device as recited in claim 10 wherein said device means is an exhaust system for causing the removal of the gas when the gas concentration exceeds said predetermined level.

14. A gas sensing and control device as recited in claim 10 wherein said device means is a computer for storing said logic signals.

15. A gas sensing and control device as recited in claim 10 further comprises manual switch means for resetting said circuit means after said device means gives said information indicating that the gas concentration has exceeded said predetermined level.

16. A gas sensing and control device as recited in claim 15 wherein said transducer means comprises a transducer which changes its conductivity in response to the amount of sensed gas; said comparator means comprises a comparator amplifier having one input coupled to an output of said transducer so as to compare the comparator voltage against a predetermined voltage level and providing a logic high signal when said comparator voltage indicates gas concentration above said predetermined gas level; buffer means and power amplifier means; said buffer means, coupled to the output of said comparator, provides a logic high signal when said transducer provides an indication that the gas exceeds said predetermined level; said power transistor being coupled to said buffer means to provide a logic high signal to close said switch means.

17. A gas sensing and control device as recited in claim 16 wherein said switch means comprises two solid state switches; said first solid state switch being capable of providing voltage to said power transistor, said devices, and said valve means; said valve means comprises a normally open valve which is closed when the gas exceeds said predetermined level.

18. A gas sensing control device as recited in claim 17 further comprises manual switch means for resetting said device after said device after said device closes the flow of gas in the conduit.

19. A gas sensing control device as recited in claim 2 further comprises manual switch means for resetting said device after said device after said device closes the flow of gas in the conduit.

20. A gas sensing and control device of the type for use with a gas conduit for channeling gas to a heating device or the like, said sensing and control device comprising:
  a) transducer means for sensing the concentration gas in the air and providing voltage indicative thereof;
  b) electronic circuit means, responsive to said transducer means, for providing at least two logic signals indicative of whether or not the concentration of the gas has exceeded a predetermined level and further comprising:
     comparator means, responsive to said transducer means, for comparing said voltage provided by said transducer with a predetermined base voltage and providing at least one logic signal indicating that the gas concentration exceeds said predetermined level of concentration;
     logic amplifier means, responsive to said comparator means, for providing one of two logic signals indicating whether the gas concentration is below or above said predetermined level; and
     switch means, responsive to said amplifier means, for causing said valve means to close the conduit when the gas concentration exceeds said predetermined level;
  b) device means, responsive to said switch means, for providing information in response to said logic signals;
  c) manual switch means for resetting said circuit means after said device means gives said information indicating that the gas concentration has exceeded said predetermined level;
  d) valve control means, operatively connected to the gas conduit and responsive to said electronic circuit means, for closing or opening the gas conduit in response to one of said two logic signals to thereby close the flow of the gas in the conduit when the gas concentration exceeds said predetermined level; and
  e) wherein said transducer means comprises a transducer which changes its conductivity in response to the amount of sensed gas; said comparator means comprises a comparator amplifier having one input coupled to an output of said transducer so as to compare the comparator voltage against a predetermined voltage level and providing a logic high signal when said comparator voltage indicates gas concentration above said predetermined gas level; buffer means and power amplifier means; said buffer means, coupled to the output of said comparator, provides a logic high signal when said transducer provides an indication that the gas exceeds said predetermined level; said power transistor being coupled to said buffer means to provide a logic high signal to close said switch means.

21. A gas sensing and control device as recited in claim 20 wherein said switch means comprises two solid state switches; said first solid state switch being capable of providing voltage to said power transistor, said devices, and said valve means; said valve means comprises a normally open valve which is closed when the gas exceeds said predetermined level.

22. A gas sensing control device as recited in claim 21 further comprises manual switch means for resetting said device after said device after said device closes the flow of gas in the conduit.

23. A gas sensing device for sensing the presence of gas and employing a source of voltage and for use in connection with a conduit carrying gas, comprising:
  a) a gas sensing transducer comprising a heating element and a sensing element; said transducer heating element being connected across the source of voltage to ground;
  c) a comparator;
  d) a resistor divider network comprising two series connected resistors coupling an output of said voltage source to ground; one input of said comparator being coupled to the junction of said two series connected resistors;
  e) said resistor divider network further comprises a third resistor for coupling the output of said source of voltage to the other input of said comparator; said sensing element of said transducer being coupled to said third resistor and said second comparator input;
  f) a fourth and fifth resistor divider network; a unit gain buffer being coupled to the output of said comparator through said fourth resistor and to ground through said fifth resistor;
  g) a sixth resistor coupled from the output to one input of said unit gain buffer to provide a threshold level for said unit gain buffer to turn ON;
  h) a power transistor having its base coupled to said unit gain buffer output;
  i) a first solid state switch coupled to the collector of said power transistor and the source of voltage;
  j) speaker means coupled by said first solid state switch to said source of supply;
  k) a normally open valve coupled through said second switch so as to be closed upon the sensing of gas above a predetermined level by said transducer;
  l) a manual switch means coupling said first solid state switch to the source of supply to be manually openable so as remove voltage from said power transistor to thereby reset the device; and
  m) warning devices coupled to at least said second solid state switch to furnish a warning that the gas has exceeded said predetermined level.

* * * * *